(12) United States Patent
Isaacs et al.

(10) Patent No.: US 8,221,746 B2
(45) Date of Patent: Jul. 17, 2012

(54) ANTIOXIDANT FOR USE IN COSMETIC, MEDICATED AND PHARMACEUTICAL PREPARATIONS

(76) Inventors: Elliot James Isaacs, London (GB); Emma Gregory, London (GB)

( * ) Notice: Subject to any disclaimer, the term of this patent is extended or adjusted under 35 U.S.C. 154(b) by 443 days.

(21) Appl. No.: 12/434,409

(22) Filed: May 1, 2009

(65) Prior Publication Data

US 2009/0274677 A1 Nov. 5, 2009

(30) Foreign Application Priority Data

May 2, 2008 (EP) ..................................... 08155616

(51) Int. Cl.
*A61K 38/43* (2006.01)
(52) U.S. Cl. ...................................................... 424/94.1
(58) Field of Classification Search ........................ None
See application file for complete search history.

(56) References Cited

U.S. PATENT DOCUMENTS

| | | | |
|---|---|---|---|
| 2003/0165444 A1* | 9/2003 | Cals-Grierson et al. | 424/59 |
| 2004/0191330 A1* | 9/2004 | Keefe et al. | 424/638 |
| 2005/0271692 A1* | 12/2005 | Gervasio-Nugent et al. | 424/401 |
| 2008/0161735 A1* | 7/2008 | Lee et al. | 601/125 |
| 2010/0063139 A1* | 3/2010 | Nizard et al. | 514/456 |

FOREIGN PATENT DOCUMENTS

| | | |
|---|---|---|
| EP | 1002533 | 5/2000 |
| EP | 1430882 | 6/2004 |
| EP | 1430933 | 6/2004 |
| WO | 0174320 | 10/2001 |
| WO | 0182888 | 11/2001 |
| WO | 2004041174 | 5/2004 |

OTHER PUBLICATIONS

Gottschalk et al., "International Cosmetic Ingredient Dictionary and Handbook"; The Cosmetic, Toiletry and Fragrance Association, Waskington D.C. (2006) p. 726, Dimethylmethoxy Chromanol; XP002501164.

Thibodeau A., "The crucial role of metalloproteinase inhibitors and regenerating antioxidants in the age-related alterations of the skin"; SOFW Journal, 131(4), 10-12, 14-16, 18-20 (2005); XP002501163.

\* cited by examiner

*Primary Examiner* — Kenneth R. Horlick
*Assistant Examiner* — David Thomas
(74) *Attorney, Agent, or Firm* — Crose Law LLC; Bradley D. Crose

(57) ABSTRACT

The invention provides the use a 2,2-dimethyl chroman as a SOD mimetic in a cosmetic preparation. Cosmetic preparations comprising a 2,2-dimethyl chroman as a SOD mimetic are described, as well as methods for treating or preventing free radical damage to skin cells and treating or preventing hair loss which comprise topical administration of a 2,2-dimethyl chroman as a SOD mimetic.

14 Claims, 2 Drawing Sheets

ANTIOXIDANT FOR USE IN COSMETIC, MEDICATED AND PHARMACEUTICAL PREPARATIONS

CROSS-REFERENCE TO RELATED APPLICATION

Pursuant to 35 U.S.C. §119 (a), this application claims priority to European Patent Application Serial No. 08155616.9 filed May 2, 2008; the disclosure of which priority application is herein incorporated by reference.

SUMMARY

The present invention relates to cosmetic, medicated and pharmaceutical preparations, in particular, antioxidants for use in cosmetic preparations. The invention provides the use a 2,2-dimethyl chroman as a SOD mimetic in a cosmetic preparation. Cosmetic preparations comprising a 2,2-dimethyl chroman as a SOD mimetic are described, as well as methods for treating or preventing free radical damage to skin cells and treating or preventing hair loss which comprise topical administration of a 2,2-dimethyl chroman as a SOD mimetic.

DETAILED DESCRIPTION

Figure 1:
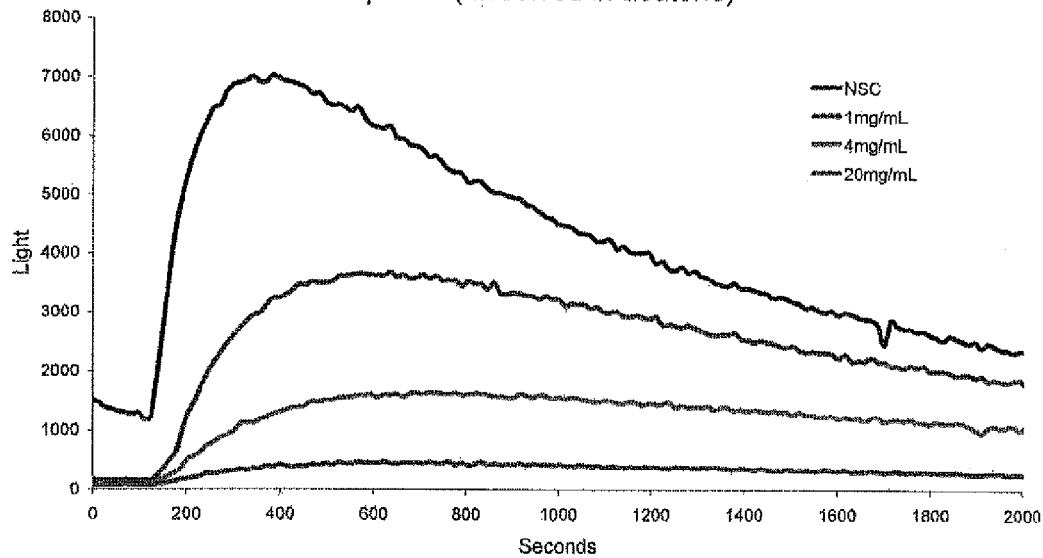
FIG. 1 is a graph showing the light response curves for 0.1% Lipochroman ("Sample 9a") in the ABEL Antioxidant Test with Enzyme Generated Superoxide. The curve with the highest peak is the no sample control. The other curves, in order of descending peak height, are 1 mg/mL, 4 mg/mL and 20 mg/mL sample.

In chemistry, radicals (often referred to as free radicals) are atomic or molecular species with unpaired electrons on an otherwise open shell configuration. These unpaired electrons are usually highly reactive, so radicals are likely to take part in chemical reactions. Radicals play an important role in combustion, atmospheric chemistry, polymerization, plasma chemistry, biochemistry and many other chemical processes, including human physiology. For example, superoxide and nitric oxide regulate many biological processes, such as controlling vascular tone. "Radical" and "free radical" are frequently used interchangeably, however a radical may be trapped within a solvent cage or be otherwise bound. Historically, the term radical has also been used for bound parts of the molecule, especially when they remain unchanged in reactions. For example, methyl alcohol was described as consisting of a methyl 'radical' and a hydroxyl 'radical'. Neither were radicals in the usual chemical sense, as they were permanently bound to each other and had no unpaired, reactive electrons. This is why the term 'free radical' has come into more common use. In mass spectrometry, such radicals are observed after breaking down the substance with a hail of energetic electrons.

Reactive oxygen species (ROS) include oxygen ions, free radicals and peroxides, both inorganic and organic. They are generally very small molecules and are highly reactive due to the presence of unpaired valence shell electrons. ROS form as a natural by-product of the normal metabolism of oxygen and have important roles in cell signalling. However, during times of environmental stress ROS levels can increase dramatically, which can result in significant damage to cell structures. This cumulates into a situation known as oxidative stress.

So, free radicals (molecules with unpaired electrons) and other reactive oxygen containing species (ROS) are highly reactive. They are continually produced in the body and are continually destroyed by a range of substances known collectively as antioxidants. They have very important functions in the body, especially those produced by white blood cells, in such activities as killing bacteria and removing foreign agents. This is especially noticeable at sites of inflammation where billions of ROS-producing white blood cells accumulate. When this happens, these reactive chemical species, together with enzymes released from granules within the white blood cells, injure or even kill cells, damage DNA and attack enzymes and other compounds. There are however other occasions, during the course of normal cell respiration for example, when free radicals and ROS are produced as by-products of cellular metabolism. Here again, in the absence of sufficient quantities of appropriate antioxidants, oxidative stress and concomitant tissue damage can occur, sometimes over a very long period of time.

Oxidative stress is thought to contribute to the development of a wide range of diseases including Alzheimer's disease, Parkinson's disease, the pathologies caused by diabetes, rheumatoid arthritis and neurodegeneration in motor neurone diseases. In many of these cases it is unclear if oxidants trigger the disease or if they are produced as a consequence of the disease and cause the disease symptoms; as a plausible alternative, a neurodegenerative disease might result from defective axonal transport of mitochondria, which carry out oxidation reactions. One case in which this link is particularly well understood is the role of oxidative stress in cardiovascular disease. Here, low density lipoprotein (LDL) oxidation appears to trigger the process of atherogenesis, which results in atherosclerosis, and finally cardiovascular disease.

Oxidative stress is bad for the skin. Free radical damage can cause deterioration of the supportive connective tissues resulting in decreased elasticity and resilience. Exposure of skin to solar ultraviolet radiation starts photochemical reactions in the skin leading to ROS formation. Sun damage produces both skin cancers as well as photo-ageing which shows itself on the skin as wrinkling, scaling, dryness and mottled pigmentation. Antioxidants play an important part in protective and repair mechanisms within the skin. Antioxidants may be consumed from food and supplements, manufactured in the skin or applied to the skin as topical preparations. The antioxidants of most significance in slowing down free radical damage to the skin are: the vitamins A, C and E, the enzyme superoxide dismutase, the group of chemical compounds known as flavonoids, and the individual chemical substances beta carotene, glutathione, selenium and zinc, among others. The relevance of the foregoing to the cosmetics industry is that there have been many studies demonstrating beneficial health effects resulting from topical application of preparations containing antioxidants. While the underlying mechanisms for these effects are not fully understood, enough is known about the distribution, activity and regulation of antioxidants in the skin to enable the development of effective pharmaceutical and cosmetic strategies involving antioxidant formulations. These developments are aimed at reducing the risk of UV induced cancers, photo aging and desquamatory skin disorders (Thiele, 2001; Thiele et al, 2001) as well as maintaining healthy skin condition and ameliorating the effects of ageing.

Antioxidants are therefore employed in skin care products to reduce and control free radicals. Antioxidants are said to complement skin care nutrients, one keeping harmful substances from destroying the skin while the other keeps the skin healthy and strong.

Critics used to claim that there was no evidence that topically based products affected skin aging. Over the years, a large number of published studies have proven the sceptics wrong. Science clearly substantiates the role that free radicals play in causing skin aging and the fact that topically applied antioxidants confer significant protection and can even partially reverse some aspects of skin aging. Indeed, various animal and human studies have proven that low molecular weight antioxidants, especially vitamins C and E, as well as alpha-lipoic acid exert protective effects against free radical damage (oxidative stress) (Podda et al, 2001).

Fitzpatrick and Rostan (2002) report a double-blind study in which a topical vitamin C complex was applied to one half of the face and a placebo gel to the opposite side. Clinical evaluation of wrinkling, pigmentation, inflammation and hydration was performed prior to the study and at weeks 4, 8, and 12. The results showed a statistically significant improvement of the vitamin C-treated side, with decreased photoaging scores of the cheeks and the perioral area. The peri-orbital area improved in both the vitamin C and placebo-gel group, probably indicating improved hydration. The overall facial improvement of the vitamin C side was statistically significant. Biopsies showed increased collagen formation in the vitamin C group. This study showed that topically applied vitamin C results in clinically visible and statistically significant improvement in wrinkling when used for 12 weeks. This clinical improvement correlated with biopsy evidence of new collagen formation.

In another randomised double-blind trial (Traikovich, 1999), human volunteers were used to determine the efficacy of topical vitamin C application in treating mild to moderate photodamage of facial skin. Methods of evaluating efficacy included an objective computer-assisted image analysis of skin surface topography, subjective clinical and photographic appearance and patient self-appraisal questionnaires. Topical vitamin C was applied to one side of each patients face and a control vehicle on the other side for 3 months. The results using the optical image analysis demonstrated that compared to the placebo-vehicle, the vitamin C-treated side of the face showed a statistically significant 71% combined score improvement. Clinical assessment parameters demonstrated significant improvement with vitamin C treatment compared to the placebo vehicle for fine wrinkling, tactile roughness, coarse rhytids, skin tone, sallowness and overall features. Patient questionnaire results demonstrated statistically significant improvement overall, with the vitamin C treatment 84.2% greater than control. Photographic assessment demonstrated significant improvement with vitamin C treatment (57.9% greater than the improvement in the control group). This 3-month study using topical vitamin C provided objective and subjective assessment of the improvement in photodamaged facial skin.

Humbert et al (2003) describe another double-blind, randomized trial which was performed over a 6-month period, comparing the action of the vitamin C cream vs. excipient on photoaged skin. Clinical assessments included evaluation at the beginning and after 3 and 6 months of daily treatment. They were performed by the investigator and compared with the volunteer self-assessment. Skin relief parameters were determined on silicone rubber replicas performed at the same time-points. Cutaneous biopsies were obtained at the end of the trial and investigated using immunohistochemistry and electron microscopy. Clinical examination by a dermatologist as well as self-assessment by the volunteers disclosed a significant improvement, in terms of the 'global score', on the vitamin C-treated side compared with the control. A highly significant increase in the density of skin microrelief and a decrease of the deep furrows were demonstrated. Ultrastructural evidence of the elastic tissue repair was also obtained and well corroborated the favourable results of the clinical and skin surface examinations. Topical application of 5% vitamin C cream was an effective and well-tolerated treatment. It led to a clinically apparent improvement of the photodamaged skin and induced modifications of skin relief and ultrastructure, suggesting a positive influence of topical vitamin C on parameters characteristic for sun-induced skin ageing.

Beitner describes another study involving alpha-lipoic acid (LA) or the reduced form dihydrolipoate (DHLA), which is a potent scavenger with anti-inflammatory properties. Previous uncontrolled studies with topical treatment with 5% LA-containing creams indicate a beneficial effect on photoageing skin. The purpose of this study was to investigate whether a cream containing 5% LA showed any advantages concerning a number of the criteria associated with ageing of the facial skin, compared with an identical cream lacking LA. Thirty-three women, mean age 54.4 years, were included in this controlled study. After randomization, half the face was treated twice daily for 12 weeks with the LA cream and the other half with the control cream. The following methods of assessment were used: self-evaluation by the test subjects, clinical evaluation, photographic evaluation and laser profilometry. Profilometry was performed before the start of treatment and at the end. All four methods of assessment showed a statistically significant improvement on the LA-treated half of the face. Laser profilometry, the most objective method used, showed an average decrease in skin roughness of 50.8% (44.9-54.0) on the LA-treated side, compared with 40.7% (32.4-48.7) on the placebo-treated half of the face $P<0.001$ (Wilcoxon matched pairs test). It is indicated that 12 weeks of treatment with a cream containing 5% LA improves clinical characteristics related to photoageing of facial skin.

Chronic inflammation is an underlying cause of common degenerative diseases. One study found that pro-oxidative factors that accelerate skin aging might activate a self-maintained micro-inflammatory process that interferes with skin elasticity and thickness. This study stated that topical antioxidants decrease this inflammatory cascade and thus afford protection to the skin structures (Giacomoni et al, 2000).

The effect of exposure to even ambient UV irradiation increases the risk for long-term, detrimental effects characterized by wrinkles and loss of skin tone and resilience. Photo-aged skin displays prominent alterations in the cellular component and the extracellular matrix of the connective tissue. UV exposure results in an accumulation of disorganized elastin and a severe loss of collagens, the major structural proteins of the dermal connective tissue. The unifying pathogenic agents for these changes are UV-generated free radicals. As well as causing permanent gene mutations, free radicals activate signal transduction pathways that are related to growth, differentiation, senescence, and connective tissue degradation (Scharfetter-kochanek et al, 2000).

Superoxide anion ($O_2^-$) is one of the main reactive oxygen species in the cell. Superoxide is highly reactive, resulting in a biological toxicity which is employed by the immune system to kill invading microorganisms: in phagocytes, superoxide is produced in large quantities by the enzyme NADPH oxidase for use in oxygen-dependent killing mechanisms of invading pathogens. The biological toxicity of superoxide is due to its capacity to inactivate iron-sulphur cluster containing enzymes (which are critical in a wide variety of metabolic pathways), thereby liberating free iron in the cell, which can undergo Fenton chemistry and generate the highly reactive hydroxyl radical. In its $HO_2$ form (hydroperoxyl radical), superoxide can also initiate lipid peroxidation of polyunsaturated fatty acids. It also reacts with carbonyl compounds and halogenated carbons to create toxic peroxy radicals. Superoxide can also react with nitric oxide (NO) to form peroxynitrite ($ONOO^-$). As such, superoxide is one of the main causes of oxidative stress. Superoxide may contribute to the pathogenesis of many diseases, and is thought to be involved also in aging via the oxidative damage that it inflicts on cells.

Because superoxide is toxic, nearly all organisms living in the presence of oxygen contain isoforms of the superoxide scavenging enzyme, superoxide dismutase, or SOD. SOD neutralizes superoxide by catalyzing its dismutation into hydrogen peroxide and oxygen. Dismutation of superoxide anions to oxygen and hydrogen peroxide occurs spontaneously, however, catalysis of the reaction by SOD is biologically necessary because the reaction of superoxide with nitric oxide radicals to form toxic peroxynitrite occurs faster that superoxide's reaction with itself (dismutation). Simply-stated, SOD outcompetes damaging reactions of superoxide, thus protecting the cell from superoxide toxicity. SOD is an extremely efficient enzyme.

SOD is a known antioxidant ingredient of cosmetic preparations, utilized for its ability to quench reactive superoxide anions. Nevertheless, SOD is expensive and there is an ongoing search for alternative compounds that neutralize superoxide in a manner which simulates the enzymic action of SOD i.e. SOD mimetics.

In view of the foregoing, there remains a need for safe and effective SOD mimetics for use as antioxidants in cosmetic preparations. It is an objective of the present invention to fulfil this need.

The present invention is based on the inventor's finding that Lipochroman-6 shows significant SOD mimetic activity i.e. Lipochroman-6 detoxifies superoxide anions in a manner that simulates the effect of SOD.

Lipochroman-6 (Lipotec S.A., Barcelona, Spain; INCI name: dimethylmethoxy chromanol) is a synthetic analogue of gamma-tocopherol known as a high potency antioxidant with specificity to inhibit peroxynitrite formation. However, SOD-mimetic activity of Lipochroman-6 has not previously been described.

Accordingly, the present invention provides the use of Lipochroman-6 as a SOD mimetic in a cosmetic preparation.

Lipochroman-6 is a 2,2-dimethyl chroman corresponding to the formula:

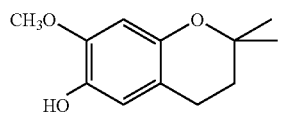

As used herein, the term "cosmetic preparations" includes, but is not limited to medicated products, medicines, cosmetics (including make-up, i.e. colour cosmetics), deodorants, antiperspirants, hair care and skin care products, and may be cleansers, moisturizers and combinations thereof. The preparations may take a variety of final forms, non-limiting examples of which include lotions, creams, emulsions, pastes, milks, liquids, gels, aerosols, solid forms, eye jellies, masks, suspensions and anhydrous liquids.

The cosmetic preparations are topically applied, i.e. directly laid on or spread on outer skin, scalp or hair, e.g. by use of the hands or an applicator such as a wipe, roller or spray.

The invention further provides a cosmetic preparation comprising Lipochroman-6 as a SOD mimetic.

Preferably, the Lipochroman-6 is present at a concentration of 0.1% or greater. The inventor has observed a significant SOD mimetic effect within this concentration range. In contrast, the dosage in the final formulation recommended by the manufacturers is 0.01 to 0.05%.

In one embodiment, the cosmetic preparation is in the form of a gel, lotion or cream suitable for application to the face, neck and other exposed areas of the body. In another embodiment, the cosmetic preparation is in the form of a lotion, cream or shampoo suitable for application to the scalp or hair.

The antioxidant capacity of the Lipochroman-6 containing cosmetic preparation may be further enhanced by the inclusion of other antioxidant compounds in the formulation. Accordingly, the cosmetic preparation of the invention may further comprise one or more additional antioxidants, for example, an antioxidant selected from a transition metal salt of PCA (e.g. copper PCA), EUK-134, propyl gallate, alpha lipoic acid, vitamin A, vitamin C and its derivatives, vitamin E, superoxide dismutase, flavonoids, beta carotene, glutathione, selenium, zinc, resveratrol, butylated hydroxytoluene (BHT), butylated hydroxyanisole (BHA), tert-butylhydroquinone (TBHQ) and ferulic acid. These ingredients augment the SOD mimetic activity of the Lipochroman-6 by broadening the spectrum of free-radical and non-radical oxidant species the preparation is capable of neutralizing, thereby providing a cosmetic preparation having exemplary antioxidant capacity.

Advantageously, the cosmetic preparation of the invention, comprising Lipochroman-6 as a SOD mimetic, further comprises a transition metal salt of PCA, such as copper PCA. Transition metal salts of PCA are exemplified herein by reference to copper PCA. Accordingly, references to copper PCA may be taken to also include pyrrolidone carboxylates of other transition metals.

As disclosed by the present inventor in co-pending UK patent application no. GB 0800749.4, copper PCA has strong and specific antioxidant activity against peroxynitrite and hydroxyl radical and also catalase mimetic activity. Accordingly, copper PCA complements the SOD mimetic activity of the Lipochroman-6 very well to provide a preparation that is particularly effective in alleviating oxidative stress. Beneficially, Lipochroman-6 does not cause a loss of antioxidant activity or undesirable smell when mixed with copper containing compounds, such as copper PCA, in a cosmetic preparation, as has been found with some SOD mimetic compounds.

Where the cosmetic preparation contains a transition metal salt of PCA, such as copper PCA, it is desirable to include a protectant/stabilizer to protect the copper PCA, i.e. to stabilize the antioxidant activity of the copper PCA. One example of a suitable stabilizer is sodium metabisulphite (SMBS). Other ingredients which may act to stabilize the antioxidant activity of a cosmetic preparation according to the invention are ferulic acid, citric acid, BHT, BHA, TBHQ, idebenone and coenzyme Q10.

Alternatively or additionally, the cosmetic preparation of the invention, comprising Lipochroman-6 as a SOD mimetic, may be prepared as an aqueous gel, in which the copper PCA is more stable (than in a cream base, that is, an oil/water emulsion). The inventors have found that Lipochroman-6, which is more oil soluble, can be solubilised within the aqueous gel to give a single phase (i.e. not comprising separate oil and water phases as in an emulsion), single formula (i.e. one part) product. In this embodiment a solubilising agent such as polysorbate 20 or others known in the art is employed which coats each oil molecule, the complex so formed being water soluble.

If a cream product is desired, the cosmetic preparation may be formulated in two parts: a first part in the form of a gel containing the copper PCA (and, optionally, other ingredients best suited to, or conveniently prepared in, aqueous formulation) and a second part in the form of a cream containing other (cream base compatible) components of the cosmetic preparation, as described in GB 0800749.4. Ideally, the copper PCA is in the aqueous gel part and the Lipochroman-6, which has a greater affinity for the oily phase, is in the cream part. Any potential undesirable reaction between the SOD mimetic Lipochroman-6 and the copper PCA is thereby avoided by keeping these components separate prior to use. Thus this two part formulation gives a two part product, the two parts being combined at the point of use.

The inventors observed that in a two part formulation as described above, there is a tendency for a minor metallic malodour caused by a reaction between the lipochroman-6 and the copper. The inventors have found that this can be prevented by lowering the pH of the copper PCA-containing aqueous part to approximately pH 3.0 or below by addition of a buffering agent or an acid such as citric acid, an alpha hydroxy acid or ascorbic acid. Lowering the pH of the aqueous solution enhances the potency of the Lipochroman-copper PCA combination when mixed. Addition of citric acid also enhances skin penetration of the preparation.

Lipochroman-6 and resveratrol have been found to work synergistically in an emulsion, increasing the independent antioxidant activity of either ingredient alone by more than 17% and also stabilising copper PCA when put into a solubilised single phase product.

Lipochroman and propyl gallate work synergistically as SOD mimetics but can lose activity in an emulsion. The inventors found that the addition of ferulic acid and/or TBHQ stabilised the emulsion. Alternatively the synergistic product could be created and phases separated by using a solubliser such as polysorbate 20.

In a preferred embodiment, the cosmetic preparation comprises lipochroman-6, copper PCA and propyl gallate as a single formula (i.e. solubilised lipochroman). Most preferably, the pH of the formula is adjusted to low pH e.g. 3.0. The pH may be adjusted e.g. with citric acid.

In another embodiment, the cosmetic preparation of the invention, comprising Lipochroman-6 as a SOD mimetic, further comprises EUK-134. EUK-134 (Atrium Biotechnologies Inc., Quebec, Canada; chemical name: ethylbisiminomethylguaiacol manganese chloride; chemical formula: $C_{16}H_{18}ClN_2O_4Mn$-$nH_2O$) is known to have SOD mimetic and catalase mimetic activity. EUK-134 therefore catalyzes the whole reaction leading to the detoxification of superoxide anions into water and oxygen. EUK-134 is self-regenerating in that the Mn atom at the active catalytic site undergoes several redox cycles during the dismutation of superoxide and scavenging of hydrogen peroxide produced thereby and returns to its original valence state Mn(III) ready to undertake another antioxidant reaction. The catalase activity of EUK-134 is particularly significant since the endogenous catalase enzyme is particularly labile when exposed to UV light. The clinical efficacy of EUK-134 has been demonstrated in various protocols (e.g. UV-induced skin erythema [Decraene et al, 2004] and UV-induced lipid peroxidation [Declercq et al, 2004]) at concentrations ranging between 0.01 and 0.05%. The inventor has found that there is no negative reaction when mixing Lipochroman-6 and EUK-134 in a cosmetic preparation i.e. the antioxidants do not compete with one another or interfere with each other's antioxidant capacity as often found when mixing antioxidant ingredients. EUK-134 would therefore combine well with the SOD mimetic Lipochroman-6 as compatible antioxidants with complementary activities in a cosmetic preparation.

In another embodiment, a cosmetic preparation according to the invention may comprise Lipochroman-6 as a SOD mimetic, copper PCA and EUK-134.

In a further embodiment, the cosmetic preparation of the invention, comprising Lipochroman-6 as a SOD mimetic, further comprises one or more low mass, lipophilic essential metalloelement complexes selected from copper (II) 3,5-diisopropylsalicylate ("DIPS"), copper (II) 3,5-dibromosalicylate ("DBS") and copper (II) 3,5-ditertiarybutylsalycilate ("DTBS"). DIPS, DBS and DTBS are known to have SOD mimetic activity (Shuff et al, 1992; Sanders et al, 2005; Wangila et al, 2006) and would therefore supplement well the SOD mimetic Lipochroman-6 in a cosmetic preparation.

A cosmetic preparation of the invention, comprising Lipochroman-6 as a SOD mimetic, may therefore further comprise one or more of DIPS, DBS and DTBS, alone or in combination with one or more of copper PCA and EUK-134.

In a still further embodiment, the cosmetic preparation of the invention, comprising Lipochroman-6 as a SOD mimetic, further comprises one or more of L-ascorbic acid, magnesium or sodium ascorbyl phosphate, ascorbyl palmitate, tetrasubstituted lipophilic ascorbate, or other form or derivative of vitamin C.

A preferred preparation comprises lipochroman-6 and ascorbic acid. More preferably, the preparation further comprises tetrasubstituted lipophilic ascorbate. Most preferably, this preparation is a single, anhydrous formula. Optionally, the preparation further comprises a second part comprising copper PCA, making a two part formula. The second part may further contain propyl gallate, in which case it also contains citric acid to lower the pH.

Another preferred preparation is a two part formula with a first part comprising solubilised lipochroman-6 and copper PCA and a second part comprising ascorbic acid and tetrasubstituted lipophilic ascorbate in an anhydrous base. The first part may further contain propyl gallate, in which case it also contains citric acid to lower the pH.

It has been found that, where the cosmetic preparation of the invention further comprises copper PCA and ascorbic acid, there is a tendency to form a precipitate and a "metallic" smell. Where it is desired to incorporate copper PCA and vitamin C in the Lipochroman-6-containing preparation of the invention, it is therefore preferable to utilise more stable forms of vitamin C such as magnesium ascorbyl phosphate or ascorbyl palmitate. Ascorbyl palmitate is particularly advantageous because this compound is fat based and therefore in a different phase when it meets the copper. Preferably, the Lipochroman-6 and ascorbic acid containing preparation further comprises one or more stabilisers such as ferulic acid, BHA, BHT, TBHQ or vitamin E.

The cosmetic preparation of the invention, comprising Lipochroman-6 as a SOD mimetic, may further comprise one or more compounds to increase cellular ascorbate levels, such as glutathione or nicotinamide. Glutathione is a reducing agent that recycles ascorbic acid from its oxidised form (dehydroascorbate) to its reduced form (ascorbate) by the enzyme dehydroascorbate reductase. Nicotinamide, also known as niacinamide, is a precursor of NADPH which is the terminal electron donor in the regeneration of ascorbate from monodehydroascorbate by monodehydroascorbate reductase. Such compounds therefore promote the formation of ascorbate.

Alpha lipoic acid is another antioxidant ingredient that may be included in the cosmetic preparation of the invention to supplement the SOD mimetic activity of Lipochroman-6. Its dithiol form, dihydrolipoic acid (DHLA), produced by enzymic reduction in the body, has enhanced antioxidant activity which is the source of its extraordinary power as a metabolic antioxidant. Two general types of antioxidants operate in biological systems: those associated mainly with a lipophilic phase (e.g. membranes or lipoproteins such as vitamin E and ubiquinols) or those which operate in aqueous phase such as ascorbate, glutathione and thioredoxin. Uniquely, lipoic acid as dihydrolipoate is able to interact with both phases and can act as an anchor of the antioxidant network. DHLA readily regenerates vitamin C from its oxidized form and spares vitamin C and vitamin E from being lost.

The cosmetic preparation of the invention may further comprise one or more compounds with vitamin E activity and/or carotenoids. Vitamin E compounds (tocopherols and tocotrienols) are fat soluble vitamins with antioxidant properties. Tocopherols, in particular d-alpha tocopherol, are multifaceted antioxidants that scavenge oxygen free radicals, lipid peroxy radicals and singlet oxygen. Carotenoids, such as β-carotene, are organic pigments that also act as antioxidants. Carotenoids may augment d-alpha tocopherol in scavenging peroxy radicals.

A further ingredient that may advantageously be incorporated in a cosmetic preparation according to the invention is butylated hydroxytoluene (BHT), also known as Butylhydroxytoluene. This lipophilic (fat-soluble) phenol is known in the food, cosmetic and pharmaceutical industries as a preservative with antioxidant properties.

As mentioned above with regard to copper PCA, a cosmetic preparation according to the invention may be formulated in two parts, an aqueous part and a cream part, with active ingredients incorporated in the aqueous part or the cream part according to each ingredient's requirements for optimum stability or compatibility, or simply according to convenience of formulation, the two parts being mixed prior to use.

In addition to the Lipochroman-6 and the optional supplementary ingredients already described, the cosmetic preparation according to the invention may further comprise additional cosmetically active agents known in the art. By "cosmetically active agent", it is meant any compound (natural or synthetic) that has a cosmetic or therapeutic effect on the skin, hair, or nails, including, but not limited to, lightening agents, darkening agents such as self-tanning agents, anti-acne agents, shine control agents, antimicrobial agents, anti-inflammatory agents, anti-mycotic agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, and agents for hair, nail, and/or skin conditioning.

Preferably, the Lipochroman-6-containing cosmetic preparation of the invention comprises between 1 and 99% of one or more silicone based oils is such as cyclomethicone or cyclopentasiloxane which act as base solvents (carriers) and emollients and impart a silky feel. Suitable silicone oils include DC-345 (Dow Corning) and Wacker-Belsil CM40 (Wacker Chemie AG). Silicone may be used with or without a carrier oil such as jojoba oil. In the solubilised aqueous formulation described above, a carrier oil such as jojoba oil is preferred over silicone. Silicone alternatives such as Lipo SFS-5 (Lipo Chemicals, Inc., Paterson, N.J.), INCI: Isododeane (and) hydrogenated polydecene (and) bis behenyl-liso-stearyl/phytosteryl dimer dilinoleyl dimer dilinoleate, may be used.

In a preferred embodiment, the cosmetic preparation additionally contains a sunscreen, which may be organic or physical. In this embodiment, the sunscreen reduces the amount of harmful UV reaching the skin, while the antioxidant Lipochroman-6, acting as a SOD mimetic, neutralizes ROS induced by UV that has got past the sunscreen and reached the skin. Thus, the antioxidant and the sunscreen complement one another to provide a particularly effective product to counter the effects of photo-ageing. The sunscreen further protects the cosmetic preparation itself, i.e. the product from UV degradation. The inventors have found ferulic acid to be a particularly advantageous supplementary ingredient of cosmetic preparations according to the invention because it acts as a UV filter and in addition acts to stabilise Lipochroman-6 in an aqueous format or in a two part cream emulsion. Accordingly, in a preferred embodiment a cosmetic preparation according to the invention comprises Lipochroman-6, one or more supplementary antioxidants such as those described herein, and ferulic acid. The further addition of a physical sunscreen such as titanium dioxide provides the additional benefit of opacifying and/or whitening the resultant product.

In a further aspect, the invention provides a method of treating or preventing damage to skin cells and/or hair follicle/dermal papilla cells associated with accumulation of reactive oxygen species, reactive nitrogen species or reactive carbonyl species such as free radicals, which comprises administration of Lipochroman-6, wherein the Lipochroman-6 acts as a SOD mimetic. Preferably the method comprises topical application of a cosmetic preparation comprising Lipochroman-6. The Lipochroman-6 may also be administered orally e.g. in tablet form as a food supplement or medicament. The method is especially suitable for the treatment of the symptoms of skin ageing associated with oxidative skin cell damage. Ageing of skin is of primary concern to anyone who is concerned about skin health. Signs of ageing include fine lines and wrinkles, brown spots and light spots, actinic keratoses (tiny rough precancerous growths), prominent jowl lines, sagging skin and a general increase in roughness and dryness of the skin. Preferably, the Lipochroman-6-containing cosmetic preparation further comprises one or more additional antioxidant ingredients as described above.

Any supplementary ingredient, or combination thereof, described herein in connection with the cosmetic preparation of the invention is equally a preferred supplementary ingredient in the above method of treating or preventing damage to skin cells associated with the accumulation of ROS.

There is evidence that SOD, and therefore SOD mimetics, can be effective in the treatment of hair loss (e.g. U.S. Pat. No. 5,470,876). Accordingly, the invention further provides a method of treating or preventing hair loss and or promoting hair regrowth, which comprises topical application of a cosmetic preparation comprising Lipochroman-6, wherein the Lipochroman-6 acts as a SOD mimetic.

As mentioned above, the capacity of a SOD mimetic such as Lipochroman-6 to detoxify superoxide is well-complemented by the peroxynitrite scavenging capacity of a transition metal salt of PCA, such as copper PCA. Furthermore, the present inventor has described in GB 0800749.4 that copper PCA additionally exhibits catalase mimetic activity in that it quenches hydrogen peroxide by converting it into water and oxygen. Accordingly, copper PCA further complements the SOD mimetic activity of Lipochroman-6 by detoxifying the reactive hydrogen peroxide produced by the Lipochroman-6-catalysed quenching of superoxide anions. Hence, it is expected that a composition comprising Lipochroman-6 as a SOD-mimetic in combination with a transition metal salt of PCA (e.g. copper PCA) will be particularly effective in the treatment of hair loss.

Accordingly, the method of treating or preventing hair loss and/or promoting hair regrowth may comprise topical application of a cosmetic preparation comprising Lipochroman-6 as a SOD mimetic and further comprising a transition metal salt of PCA, such as copper PCA. Optionally, the preparation further comprises one or more ingredients selected from: SOD or SOD mimetic, and catalase or catalase mimetic. In a preferred embodiment, the method of treating or preventing hair loss comprises topical application of a cosmetic preparation comprising Lipochroman-6 and copper PCA in which the Lipochroman-6 acts as a SOD mimetic and the copper PCA scavenges peroxynitrite and also detoxifies $H_2O_2$ produced as a by-product of superoxide quenching. The cosmetic preparation may further comprise one or more additional antioxidant ingredients as described supra such as propyl gallate. The copper PCA and propyl gallate may be administered in the same preparation as the lipochroman-6, or one or both of them may be administered in one or more sequentially applied preparations. If the lipochroman-6, copper PCA and propyl gallate formulated together in a single preparation, the pH is ideally adjusted to 3 or below, preferably using citric acid.

The combined activities of a SOD mimetic such as Lipochroman-6 and a catalase mimetic such as copper PCA, as described above, together result in the generation of free oxygen molecules. Preparations comprising Lipochroman-6 and copper PCA will, therefore, have utility in cosmetic products designed to promote the free $O_2$ (molecular oxygen) content of the skin.

It is known to use minoxidil as part of a treatment for hair loss, to stimulate hair regrowth. Minoxidil produces nitric oxide, a chemical messenger, which is known to be a hair follicle stimulator. It is also known no that peroxynitrite is a free radical that is damaging to hair follicles and further that peroxynitrite radicals are produced from the reaction of nitric oxide with superoxide anions. It has been shown that SOD alone or co-administered with minoxidil benefits the hair regrowth in two ways and therefore has a double effect. Firstly, it reduces the amount of superoxide anion capable of reacting with the nitric oxide thereby retaining levels of nitric oxide; and secondly, it reduces the amount of peroxynitrite produced from the superoxide/nitric oxide reaction.

If, instead of SOD, you used an antioxidant without the ability to quench superoxide anion, you would be addressing the damaging species produced by the superoxide/nitric oxide reaction, namely peroxynitrite, but not promoting retention of high levels of nitric oxide by preventing the reaction itself. In view of the foregoing, it seems that you need to use SOD or a mimetic to achieve the best results, however, two problems remain: firstly, how to remove any damaging peroxynitrite resulting from the deliberate (and desired) raising of nitric oxide levels, where SOD has little effect; and secondly, how to remove the other ROS, hydrogen peroxide, formed by the action of SOD on the superoxide anion. A preparation comprising Lipochroman-6 as a SOD mimetic and a transition metal salt of PCA solves both these problems, because a transition metal salt of PCA (such as copper PCA) has specific high quenching activity against peroxynitrite (the radical especially of interest given supplementation of precursor nitric oxide levels) providing protection from the by-product of the SOD and nitric oxide reaction, plus it will remove the ROS hydrogen peroxide by way of its catalase mimetic properties described herein. A composition comprising a combination of Lipochroman-6 as SOD mimetic and a transition metal salt of PCA (such as copper PCA) enables the double action SOD mimetic to be used without giving rise to the negative effects of hydrogen peroxide or peroxynitrite production, both of which are damaging to hair follicle cells as explained above. Simply put, the PCA salt offers a protective effect to the SOD mimetic Lipochroman-6 ingredient.

The Lipochroman-6-containing composition for the treatment of hair loss, optionally comprising a transition metal salt of PCA, may further comprise, or be co-administered with, one or more known agents for the treatment of hair loss such as minoxidil and spironolactone.

A cosmetic preparation according to the invention for use in the treatment of prevention of hair loss and/or promotion of hair loss may further comprise one or more supplementary actives known to be beneficial in the treatment of hair loss or the promotion of hair growth such as taurine, caffeine, saw palmetto, *Pygeum africanum, Urtica dioica*, minoxidil, azelaic acid, marine cartilage, hydrolysed keratin, biotin, niacin, panthenol, vitamin B6, zinc, copper peptides, horsetail silica, beta sitosterols, pycnogenol, white lupin, pumpkin seed, PABA, green tea extract, folic acid, iron, L-cysteine, magnesium and ginseng and/or one or more antioxidants selected from those listed herein.

Any supplementary ingredient, or combination thereof, described herein in connection with the cosmetic preparation of the invention is equally a preferred supplementary ingredient in the above described method of treating or preventing hair loss.

The SOD mimetics DIPS, DBS and DTBS may be particularly advantageous as supplementary antioxidant ingredients in the preparation of the invention, when used for the treatment of hair loss, because DIPS has been shown to protect nitric oxide from destruction by superoxide anion (MacKenzie et al, 1999).

Lipochroman-containing preparations according to the invention may further comprise, or be administered in combination with, WNT proteins. These are signalling molecules involved in wound healing. WNT stimulation of new hair regrowth and lipochroman work synergistically to enhance the possibility of hair regrowth as the SOD mimetic activity of lipochroman increases the presence of nitric oxide.

The efficacy of a cosmetic preparation according to the invention for treating or preventing hair loss and/or promotion of hair regrowth may be enhanced by topically administering said cosmetic preparation in combination with use of a device, such as a microneedle roller, which causes skin trauma thereby causing the release of hair-regenerative WNT proteins. Such a device can also increase the transcutaneous penetration of the cosmetic preparation to the dermal-epidermal junction (DEJ), between 0.2 and 3 mm beneath the skin surface, thought to be the site of WNT protein release.

Similarly a cosmetic preparation according to the invention may be efficacious for treating or preventing damage to skin cells or promoting the production or stimulation of structural proteins such as collagen or elastin, when said cosmetic preparation is topically administered in combination with use of a device, such as a microneedle roller, as described above, which stimulates the release of tissue-regenerative WNT proteins.

Preferred features of different aspects of the invention are as to each other *mutatis mutandis*.

The antioxidant capacity of ingredients and cosmetic preparations according to the invention can be determined using standardised commercially available test kits. A number of tests are available for determining antioxidant capacity, including ORAC (Oxygen Radical Absorbance Capacity) and ABEL (Analysis By Emitted Light) antioxidant assays. The ORAC assay developed at The National Institute on Aging, Maryland, U.S. measures the effect of a test sample on the oxidative degradation of fluorescein after being mixed with a peroxyl radical. The fluorescent intensity of the fluorescein decreases as it gets oxidised; the oxidative decay of the fluorescein is less rapid if there are antioxidants in the sample under test. The antioxidant capacity is expressed as an ORAC value relative to a standard antioxidant (trolox, a vitamin E analogue). The ABEL® antioxidant test kits available from Knight Scientific Limited (Plymouth, UK) utilise Pholasin®, the photoprotein from the bioluminescent mollusc *Pholas dactylus*, which emits light when challenged with various free radicals and other reactive oxygen containing species (ROS) (Knight, 2005; Knight et al, 2007). If a material to be tested for potential antioxidant capacity is challenged with one or more of these reactive species in the presence of Pholasin, then any antioxidants in the sample will compete with Pholasin. The result of this competition is a reduction in the amount of light emitted and sometimes, in addition, a delay in the time at which the maximum light emitted occurs. A light response curve is produced for each sample tested.

Other tests for measuring antioxidant activity are described in Schlesier et al (2002), namely Trolox equivalent antioxidant capacity assay (TEAC I-III assay), Total radical-trapping antioxidant parameter assay (TRAP assay), 2,2-diphenyl-1-picrylhydrazyl assay (DPPH assay), N,N-dimethyl-p-phenylendiamine assay (DMPD assay), Photochemiluminescence assay (PCL assay) and Ferric reducing ability of plasma assay (FRAP assay).

The antioxidant capacity of Lipochroman-6-containing samples and comparative samples was determined using the ABEL-Antioxidant Test With Enzyme Generated Superoxide (Knight Scientific Limited, Plymouth, UK). This test measures the activity of superoxide or superoxide dismutase against the test samples. In this assay, superoxide is produced enzymatically and at constant rates, mimicking the behaviour of enzymes in living cells. Superoxide is produced as a by-product of the production of uric acid from the enzyme-catalysed oxidation of xanthine with xanthine oxidase. The assay is used as an antioxidant test and for measuring the activity of superoxide dismutase (SOD). The assay can be used to quantify the superoxide produced by cells as well as assessing the antioxidant capacity of samples.

The activity of SOD and mimetics of this enzyme can be readily quantified. As SOD will compete with Pholasin for any superoxide produced in the x/xo system, less light will be emitted in the presence of SOD. From a set of SOD standards, the amount of SOD or a mimetic of SOD in a sample under test can be determined by the amount of light emitted in the presence of Pholasin.

The invention is illustrated by the following non-limiting example which make reference to the figures, of which:—

FIG. 1 is a graph showing the light response curves for 0.1% Lipochroman ("Sample 9a") in the ABEL Antioxidant Test with Enzyme Generated Superoxide. The curve with the highest peak is the no sample control. The other curves, in order of descending peak height, are 1 mg/mL, 4 mg/mL and 20 mg/mL sample.

Figure 2:
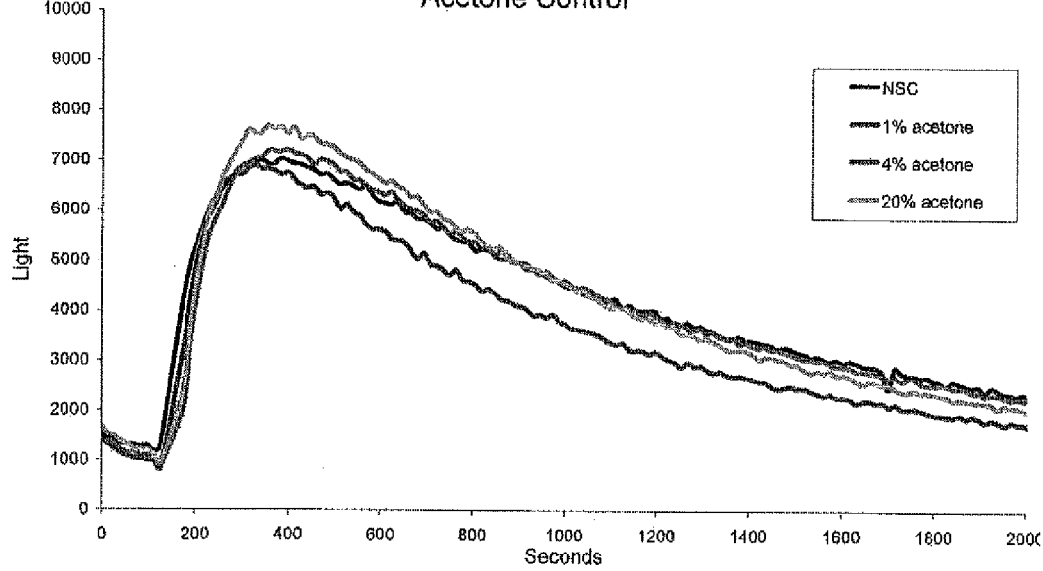
FIG. 2 is a graph showing the light response curves for acetone control in the ABEL Antioxidant Test with Enzyme Generated Superoxide. The graph shows curves for: no sample control (third highest peak), 1% acetone (lowest peak), 4% acetone (second highest peak) and 20% acetone (highest peak).

FIG. 2 is a graph showing the light response curves for acetone control in the ABEL Antioxidant Test with Enzyme Generated Superoxide. The graph shows curves for: no sample control (third highest peak), 1% acetone (lowest peak), 4% acetone (second highest peak) and 20% acetone (highest peak).

Figure 3:
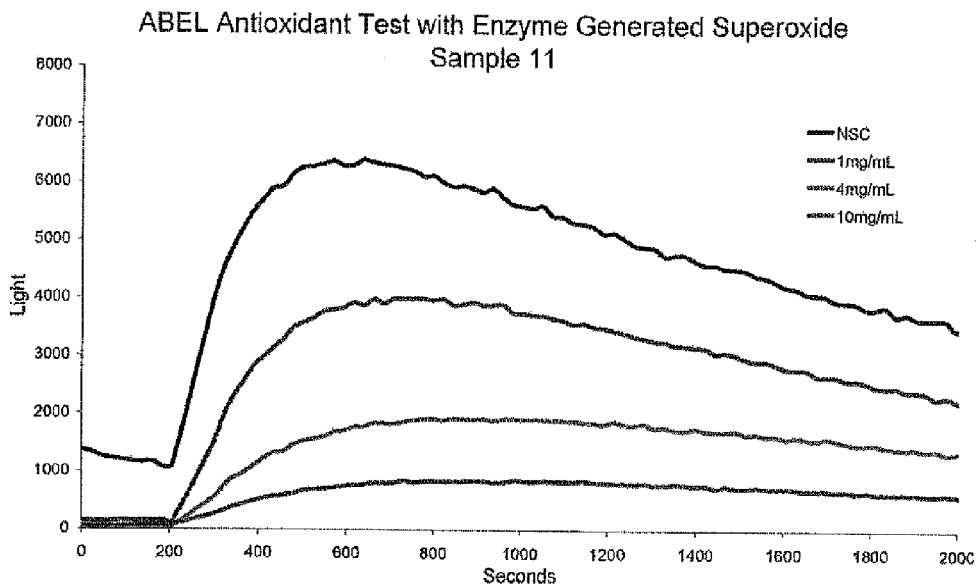
FIG. 3 is a graph showing the light response curves for 0.05% EUK-134 and 0.1% Lipochroman in cream base ("Sample 11") in the ABEL Antioxidant Test with Enzyme Generated Superoxide. The curve with the highest peak is the no sample control. The other curves, in order of descending peak height, are 1 mg/mL, 4 mg/mL and 10 mg/mL sample.

FIG. 3 is a graph showing the light response curves for 0.05% EUK-134 and 0.1% Lipochroman in cream base ("Sample 11") in the ABEL Antioxidant Test with Enzyme Generated Superoxide. The curve with the highest peak is the no sample control. The other curves, in order of descending peak height, are 1 mg/mL, 4 mg/mL and 10 mg/mL sample.

Figure 4:
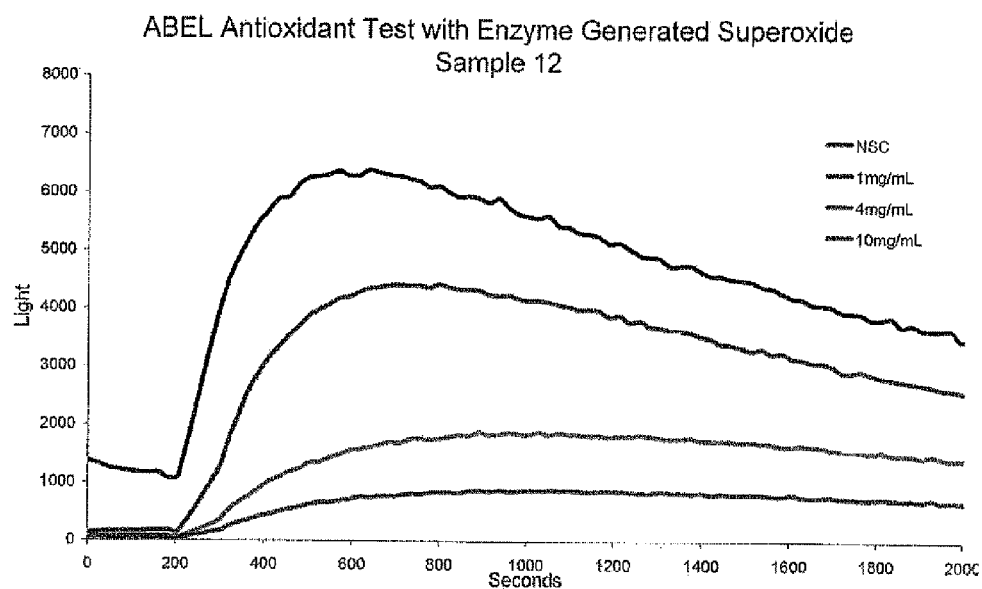
FIG. 4 is a graph showing the light response curves for 0.1% Lipochroman and peptide base cream ("Sample 12") in the ABEL Antioxidant Test with Enzyme Generated Superoxide. The curve with the highest peak is the no sample control. The other curves, in order of descending peak height, are 1 mg/mL, 4 mg/mL and 10 mg/mL sample.

FIG. 4 is a graph showing the light response curves for 0.1% Lipochroman and peptide base cream ("Sample 12") in the ABEL Antioxidant Test with Enzyme Generated Superoxide. The curve with the highest peak is the no sample control. The other curves, in order of descending peak height, are 1 mg/mL, 4 mg/mL and 10 mg/mL sample.

EXPERIMENTAL

Methods

Samples were assayed using the ABEL Superoxide and SOD quantification kit with Pholasin®, xanthine & xanthine oxidase (Knight Scientific Ltd, Plymouth, UK), according to the manufacturer's instructions.

Briefly:—The assay was performed in a microplate using a microplate luminometer. The assay reagents were as follows (per well):

100 µL assay buffer+10 µL sample
50 µL reconstituted Pholasin (10 µg/mL in assay buffer)
20 µL reconstituted xanthine (16 mM in xanthine reconstitution buffer)

Superoxide was generated by injection of 20 µL of 10.25 mU/mL xanthine oxidase into each well. [A delay in injection of xanthine oxidase allows basal chemiluminescence to be determined.]

Light was measured for 0.5 to 1.0 second in each well. The assay was run for at least 30 minutes.

The samples tested are shown in Table 1.

TABLE 1

| Sample Code | Sample Description |
| --- | --- |
| 9a* | 0.1% solution in pure soya bean oil of Lipochroman |
| 11 | 0.05% EUK-134 and 0.1% Lipochroman in cream base |
| 12 | 0.1% solution in pure soya bean oil of Lipochroman and peptide cream base |

Preparation of Samples for Assay is Described in Table 2.

TABLE 2

| Sample Code | Properties | Solvent for initial conc. |
|---|---|---|
| 9a* | Clear liquid (n.b. container leaking) | Acetone |
| 11 | Off-white cream with several brown bits | Assay buffer |
| 12 | White cream | Assay buffer |

*The solvent acetone has a significant effect on this assay. In order to reduce this effect, sample 9a was first dissolved in acetone and then further dilutions were prepared in assay buffer. As a control, a matching series of solvent-only dilutions in assay buffer was prepared.

Results

Light response curves for the samples under test are shown in FIGS. 1 to 4. In each assay, the time of injection of xanthine oxidase is easily identifiable by the change in the shape of the curve between 100 and 200 seconds.

Relative Antioxidant Capacity (RAC): ABEL-RAC Scores

By running a range of concentrations of material to be tested, the concentration of material able to reduce the light by half, the effective concentration ($EC_{50}$) of the sample, is determined. The greater the amount of material required to reduce the light by half, the weaker the antioxidant capacity. Therefore high $EC_{50}$ values indicate low antioxidant capacity.

ABEL-RAG scores are the reciprocal of the $EC_{50}$ multiplied by 100; the higher the ABEL-RAC score, the higher the antioxidant capacity of the sample.

The most usual way of expressing the score is in terms of weight. Thus: ABEL-RAC mg. However, simple calculations will lead to the very useful parameters, ABEL-RAC cost and ABEL-RAC dose.

ABEL-RAC scores for the samples tested are shown in Table 3.

TABLE 3

| Sample | Solvent | EC50 (mg/ml) | ABEL-RAC per mg dried powder | SOD Equivalent Units (mU/mg) |
|---|---|---|---|---|
| 9a* | Acetone | 0.15 | 653 | 2067 |
| 11 | Assay buffer | 0.21 | 484 | 1767 |
| 12 | Assay buffer | 0.25 | 396 | 1400 |

Discussion

In the enzyme-generated superoxide test, Lipochroman-6 showed a high antioxidant capacity: ABEL-RAC 653 per mg; 2067 SOD equivalent units (Sample 9a: FIG. 1, Table 3). Light response curves for acetone-only control samples (FIG. 2) show that the antioxidant effect observed for Lipochroman-6 is a true result and not an artefact of the acetone solvent. Although slightly reduced, the SOD mimetic activity of Lipochroman-6 remained high when the ingredient was prepared in a peptide base cream (Sample 12: FIG. 4).

The combination of Lipochroman-6 and EUK-134 in a cream base gave particularly good results: apparently a greater SOD mimetic activity than simply the additive effect of the two ingredients (Sample 11: FIG. 3, Table 3).

REFERENCES

Beitner H. Randomized, placebo-controlled, double blind study on the clinical efficacy of a cream containing 5% alpha-lipoic acid related to photoageing of facial skin. Department of Dermatology, Karolinska Hospital, 17176 Stockholm, Sweden.

Decraene, D et al (2004) A synthetic superoxide dismutase/catalase mimetic (EUK-134) inhibits membrane-damage-induced activation of mitogen-activated-protein kinase pathways and reduces p53 accumulation in ultraviolet B-exposed primary human keratinocytes. The Journal of Investigative Dermatology 122(2): 484-491.

Declercq, L et al (2004) Use of the synthetic superoxide dismutase/catalase mimetic EUK-134 to compensate for seasonal antioxidant deficiency by reducing pre-existing lipid peroxides at the human skin surface. International Journal of Cosmetic Science 26: 255-263.

Fitzpatrick R E and Rostan E F (2002) Double-Blind, Half-Face Study Comparing Topical Vitamin C and Vehicle for Rejuvenation of Photodamage. Dermatologic Surgery 28(3): 231-236.

Giacomoni et al (2000) Aging of human skin: review of a mechanistic model and first experimental data. IUBMB Life 49(4): 259-63.

Humbert PG et al (2003) Topical ascorbic acid on photoaged skin. Clinical, topographical and ultrastructural evaluation: double-blind study vs. placebo. Exp Dermatol. 12(3): 237-44.

Knight, J (2005) Pholasin-Based Antioxidant Assays for Cosmetics, Cosmeceutical and Neutraceutical Product Development. Cosmetic Science Technology 2005: 249-257.

Knight J, Knight R and Armstrong K (2007) ABEL-RAC Antioxidant scores for Quality Control of Ingredients and Quality Assurance of Products. Cosmetic Science Technology 2007: 203-213.

MacKenzie A et al (1999) Effects of superoxide dismutase mimetics on the activity of nitric oxide in rat aorta. British Journal of Pharmacology 127: 1159-1164.

Podda et al (2001) Low molecular weight antioxidants and their role in skin ageing. Clin Exp Permatol 26(7): 578-82.

Scharfetter-kochanek et al (2000) Photoaging of the skin from phenotype to mechanisms. Exp Gerontol 35(3): 307-16.

Schlesier K et al (2002) Assessment of Antioxidant Activity by Using Different In Vitro Methods. Free Radical Research 36(2): 177-187.

Sanders et al (2005) The superoxide dismutase-like activity of copper (II) 3,5-dibromosalicylate. Arkansas Academy of Science 89$^{th}$ Annual Meeting Apr. 8 and 9, 2005 at Hendrix College.

Shuff S T et al (1992) Stable superoxide dismutase (SOD)-mimetic ternary human serum albumin-Cu(II)(3,5-diisopropylsalicylate)2/Cu(II)2(3,5-diisopropylsalicylate)4 complexes in tissue distribution of the binary complex. Biochem Pharmacol. 43(7): 1601-12.

Thiele, J J (2001) Oxidative Targets in the Stratum Corneum. Skin Pharmacology & Applied Skin Physiology 14: 87-91.

Thiele, J J, Schroeter C, Hsieh S N, Podda M, Packer L (2001) The Antioxidant Network of the Stratum Corneum. Curr Probl Dermatol 29: 26-42.

Traikovich S S (1999) Use of topical ascorbic acid and its effects on photodamaged skin topography. Arch Otolaryngol Head Neck Surg. 125: 1091-1098.

Wangila, G W et al (2006) Prevention of cysplatin-induced kidney epithelial cell apoptosis with a Cu superoxide dismutase-mimetic [copper$^{II}{}_2$(3,5-ditertiarybutylsalycilate)$_4$(ethanol)$_4$]. Toxicology in Vitro 20(8): 1300-12.

The invention claimed is:

1. A cosmetic preparation comprising Lipochroman-6 (dimethyl methoxychromanol) as an antioxidant, wherein the Lipochroman-6 acts as a superoxide dismutase (SOD) mimetic, characterised in that the preparation further comprises one or more supplementary antioxidants selected from the group of catalase mimetics and derivatives thereof consisting of transition metal salts of PCA (pyrrolidone carboxylic acid), EUK-134 (chloro[[2,2'-[1,2-ethanediylbis[nitrilo-κN)methylidyne]]bis[6-methoxyphenolato-κO]]]-manganese), and propyl gallate.

2. A cosmetic preparation as claimed in claim 1, in which the supplementary antioxidant is a transition metal salt of PCA.

3. A cosmetic preparation according to claim 2, in which the transition metal salt of PCA is a copper PCA.

4. A cosmetic preparation according to claim 1, in which the supplementary antioxidant is EUK-134.

5. A cosmetic preparation according to claim 1, which is a gel, cream, shampoo or anhydrous preparation.

6. A cosmetic preparation according to claim 1, in which the concentration of Lipochroman-6 is 0.1% or greater.

7. A cosmetic preparation as claimed in claim 1, in which the cosmetic preparation is formulated in two parts comprising a first aqueous part and a second part comprising a cream or anhydrous base.

8. A cosmetic preparation as claimed in claim 7, in which the first part is an aqueous gel comprising copper PCA and the second part is a cream or anhydrous base.

9. A cosmetic preparation as claimed in claim 8, in which the first part comprises solubilised lipochroman-6 and one or more of copper PCA, propyl gallate and citric acid, and the second part comprises ascorbic acid and/or tetrasubstituted lipophilic ascorbate in an anhydrous base.

10. A cosmetic preparation as claimed in claim 1, in which the pH of the cosmetic preparation is adjusted to 3 or below.

11. A cosmetic preparation as claimed in claim 1, wherein the cosmetic preparation further comprises copper PCA and propyl gallate at a reduced pH.

12. A cosmetic preparation as claimed in claim 1, wherein the cosmetic preparation further comprises a stabilizer selected from the group consisting of ferulic acid, butylated hydroxytoluene (BHT), butylated hydroxyanisole (BHA), tert-butylhydroquinone (TBHQ), sodium metabisulphite (SMBS) and vitamin E.

13. A cosmetic preparation as claimed in claim 1, wherein the cosmetic preparation further comprises one or more supplementary actives known to be beneficial in the treatment of hair loss or the promotion of hair growth selected from the group consisting of taurine, caffeine, saw palmetto, *Pygeum africanum*, Urtica dioica, minoxidil, azelaic acid, marine cartilage, hydrolysed keratin, biotin, niacin, panthenol, vitamin B6, zinc, copper peptides, horsetail silica, beta sitosterols, pycnogenol, white lupin, pumpkin seed, PABA, green tea extract, folic acid, iron, L-cysteine, magnesium and ginseng.

14. A cosmetic preparation as claimed in claim 1 further comprising ascorbic acid and/or tetrasubstituted lipophilic ascorbate in a single anhydrous formula.

\* \* \* \* \*